US006030950A

United States Patent [19]
Ohlenschläger

[11] Patent Number: 6,030,950
[45] Date of Patent: *Feb. 29, 2000

[54] PHARMACEUTICAL THERAPEUTIC USE OF GLUTATHIONE DERIVATIVE

[76] Inventor: Gerhard Ohlenschläger, Hauptstrasse 22, D-6240 Köigstein, Germany

[ * ] Notice: This patent issued on a continued prosecution application filed under 37 CFR 1.53(d), and is subject to the twenty year patent term provisions of 35 U.S.C. 154(a)(2).

[21] Appl. No.: 08/915,449

[22] Filed: Aug. 20, 1997

Related U.S. Application Data

[63] Continuation of application No. 08/599,280, Feb. 9, 1996, abandoned, which is a continuation of application No. 08/341,028, Nov. 17, 1994, abandoned, which is a continuation of application No. 08/214,035, Mar. 16, 1994, abandoned, which is a continuation of application No. 08/089,954, Jul. 12, 1993, abandoned, which is a continuation of application No. 07/985,302, Dec. 4, 1992, abandoned, which is a continuation of application No. 07/869,776, Apr. 16, 1992, abandoned, which is a continuation of application No. 07/728,717, Jul. 16, 1992, abandoned, which is a continuation of application No. 07/334,376, Mar. 28, 1989, abandoned.

[30] Foreign Application Priority Data

Jul. 9, 1987 [DE] Germany ............................. 37 22 647

[51] Int. Cl.$^7$ ............................. A61K 38/00; C07K 5/00; C07K 7/00
[52] U.S. Cl. ............................. 514/18; 530/331; 530/332
[58] Field of Search ..................................... 530/331, 304, 530/332; 514/18

[56] References Cited

U.S. PATENT DOCUMENTS

| 2,760,956 | 8/1956 | Brick ........................................ 530/332 |
| 3,950,387 | 4/1976 | Joullie et al. ............................. 530/331 |
| 3,984,569 | 10/1976 | Kalopissis et al. ...................... 514/562 |
| 4,618,669 | 10/1986 | Dereu et al. ............................. 530/331 |
| 4,900,719 | 2/1990 | Means et al. ............................. 514/18 |
| 5,232,913 | 8/1993 | Ohmori et al. ........................... 514/18 |
| 5,238,683 | 8/1993 | Crystal ..................................... 514/18 |

OTHER PUBLICATIONS

Berkow et al, *The Merck Manual*, Table 262–1 (1982).
Perchellet et al, *Cancer Res.* 47:477–485 (1987).
Novi et al, *Science* 212:541–542 (May 1981).
Anderson et al, *Arch. Biochem. Biophys.* 239:538–548 (1985).
Vince et al, *Biochem. Biophys. Res. Comm.* 35:593–598 (1969).

*Primary Examiner*—Avis M. Davenport
*Attorney, Agent, or Firm*—Alston & Bird LLP

[57] ABSTRACT

Methods of adjusting or maintaining the intracellular levels of glutathione of a subject are provided. The subject is treated by administering an effective amount of an acetyl derivative of glutathione.

10 Claims, 1 Drawing Sheet

PHARMACEUTICAL THERAPEUTIC USE OF GLUTATHIONE DERIVATIVE

This application is a continuation of application Ser. No. 08/599,280, filed Feb. 9, 1996 and now abandoned, which is a continuation of Ser. No. 08/341,028, filed Nov. 17, 1994 and now abandoned, which is a continuation of Ser. No. 08/214,035, filed Mar. 16, 1994 and now abandoned, which is a continuation of Ser. No. 08/089,954, filed Jul. 12, 1993 and now abandoned, which is a continuation of Ser. No. 07/985,302, filed Dec. 4, 1992 and now abandoned, which is a continuation of Ser. No. 07/869,776, filed Apr. 16, 1992 and now abandoned, which is a continuation of Ser. No. 07/728,717, filed Jul. 11, 1991 and now abandoned, which is a continuation of Ser. No. 07/334,376, filed Mar. 28, 1989 and now abandoned.

BACKGROUND INFORMATION AND PRIOR ART

All more highly organized, multicellular, living systems, even man, cover the energy requirement of their living cells and tissue according to the principle of biological oxidation.

Carbohydrates, amino acids, fatty acids and nucleotides, on dehydrogenation (dehydrogenation=oxidation) give up by different metabolic pathways a portion of the chemical energy stored in these molecules and are finally supplied to the common final degradation in the citric acid cycle.

In the metabolic cycle of healthy cells or tissue, which represents the common final step for monosaccharides, fatty acids and amino acids, the C-6 compounds (citric acid) entering the cycle are broken down during one run in the cycle by two decarboxylation reactions to C-4 compounds (oxalacetic acid). In other words, the carbon chain is shortened by two carbon atoms.

In addition, 8 hydrogen atoms are oxidized in the citric acid cycle over the respiratory chain with production of energy to four molecules of water.

The hydrogen, obtained during dehydrogenations by various breakdown paths, is transported by hydrogen-transporting coenzymes NAD and FAD to the inner membrane of the mitochondria, the cell organelles, which are regarded as the power plants of a cell. With the structure-bound enzymes of the respiratory chain, the cytochromes, the hydrogen forms an electron transporting chain which—as also the whole of the metabolism—can function only if the hydrogen in the last element of the chain can react in a redox reaction with oxygen to form water. At a pH of 7, the normal potential $E_2$ of this redox reaction is of the order of ±0.810 volt at a pH of 7, so that a drag is exerted on the electron transport chain.

Oxygen thus is the terminal hydrogen or electron acceptor in the metabolic process and, due to its presence, maintains the flow of electrons in the metabolism of a cell.

The respiratory chain in the mitochondria thus leads to a type of biochemical oxyhydrogen gas reaction, in which the respiratory substrates are dehydrogenated. The high reaction enthalpy, which is given off when water is formed from hydrogen and oxygen, is released gradually by the stepwise reaction of the hydrogen or the electrons over a cascade of intermediate carriers and a considerable proportion is stored in the form of chemical energy as adenosine triphosphate (ATP) for energy-consuming cell reactions.

Every healthy cell, which has mitochondria, covers its energy requirements in this fashion. The number of mitochondria per cell varies between $10^2$ and $6\times10^3$, depending on the metabolic tasks, and their oxygen requirement is also correspondingly different.

In every second of the life of a living, oxidizing system, oxygen must be available to a sufficient extent in the mitochondria of all living cells. Required for this is a steady, undisturbed flow of oxygen from the respired air with an adequate partial pressure of oxygen over the respiratory passages, the transfer of oxygen at the lung-blood barrier of the lung alveoli, the diffusion through the erythrocyte membrane, the oxyhemoglobin formation and the detachment form hemoglobin in the blood capillaries of the tissue, the oxygen diffusion through the intercellular space, the interstitial space, through the cell membrane and the mitochondrial membrane up to the above-described respiratory chain. A long, but important path of the oxygen.

This oxidation, which takes place constantly undisturbed in all cells, is the important prerequisite for maintaining the health of the organism. In an approximate comparison with electrical or electronic components and their circuits, it is possible to speak of the operating characteristic curve of a healthy cell. On this curve, there is an optimum operating point, which may shift only slightly on the operating characteristic curve. If the operating point is impermissibly far removed from its optimum, then this is an indication of an appreciable malfunction of the metabolism of the cell. Such a malfunction is caused, for example, by the phenomenon of hyperoxidation, whicn is also referred to as oxidative stress. The oxidative stress may arise either through an excessive supply of activated oxygen steps (oxygen radicals) and/or through a decrease in those molecules, which normally are capable of intercepting this radical energy and are referred to as scavenger molecules. If the cells are incapable of eliminating this malfunction by their own efforts, destruction of biomolecules and cell structures, such as lipid peroxidation of the cell membranes, as well as diverse cell malfunctions, cancerous degeneration of a cell and finally cell destruction take place.

In living systems, nature had to protect its molecular and cell structures from the very start against the action of destructive oxygen radicals, which are constantly formed by exogenous noxious agents and also in cell metabolism. For this purpose, it developed protective enzymes and protective molecules as scavengers, which are capable of intercepting these radicals reliably and quickly.

As a consequence of the inability of the individual malfunctioning cells to intercept the energy-rich radicals, diseases may arise such as cancer of any origin, malignant diseases of blood cells, hepatopathies, fatty degeneration of the liver, fatty cirrhosis, liver cirrhoses of any origin, malfunctions of immunological defense functions in the area of natural killer cells, complex malfunctions of the lymphokine biosynthesis in the T helper cells, cardiomyopathies of any origin, neurological diseases of inflammatory, allergic or degenerative origin, blood cell diseases, injuries to the eye lens, proliferation and differentiation disorders of epithelial and endothelial tissue and of mucous membrane tissue and many more. The type of disease that will occur depends mainly on which cells or cell tissues are affected most severely.

It follows from this that oxidations, which are necessarily essential to the living systems, must not lead to hyperoxidations.

From a chemical point of view, oxidation means:

1. emission of electrodes,
2. emission of hydrogen,
3. absorption of oxygen.

Correspondingly, reduction means:

1. absorption of electrons
2. absorption of hydrogen,
3. emission of oxygen.

Thermodynamically all reductions are endothermic processes and all oxidations exothermic processes. This means that the oxidized stage is in a lower energy state than the reduced state. The reduced stage can emit "energy"= electrons and the oxidized stage is reduced by the "absorption of energy", that is, by the absorption of electrons.

The basis for all the reductive power in the blood and in most of the cells of man and mammals is the reduced form of the tripeptide, glutathione (G—SH) consisting of the three amino acids, glutamic acid, cystaine and glycine with the following structure formula:

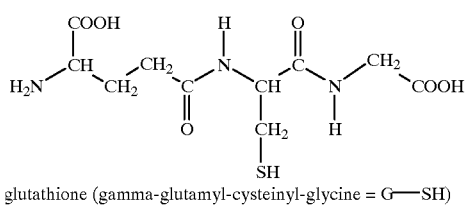

glutathione (gamma-glutamyl-cysteinyl-glycine = G—SH)

The functionality of living systems, which is based on the principle of biological oxidation, is possible only due to the existence of a reductive protection by this important molecule, G—SH.

By dehydrogenation or oxidation, two molecules of reduced glutathione (G—SH) can be converted into one molecule of oxidized glutathione (G—S—S—G) with the formation of a disulfide bond.

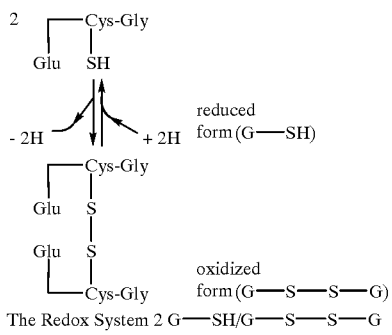

The Redox System 2 G—SH/G—S—S—G

In numerous observations, it was possible to observe that cells, which fulfill their specific function perfectly, have a concentration ratio of reduced glutathione (G—SH) to oxidized glutathione (G—S—S—G) of about 400 to 1. This means that the intact, viable cell has a high reductive potential in the form of the reduced glutathione content. The concentration ratio of G—SH to G—S—S—G in the area of 400 to 1 can be taken as an indicator of the optimal functioning and of the reliable maintenance of the structure of the cell.

The reductive potential of the reduced glutathione, that is, the optimum, high, intracellular concentration of this material, is of the utmost importance for maintaining the functionality of many and perhaps even all enzymes of the cell metabolism, for preventing oxidative changes in the catalytic and allosteric centers of the enzymes and for maintaining their optimum conformation.

All presently existing classical therapies support either the phenomenon of oxidation, that is, the oxidative side of living systems, or, through drugs which, as xenobiotics, require oxidation for their degradation and for metabolite formation, intervene in the "oxidative power" of the metabolism, such as the cytochrome-p-450 system and drug degradation.

OBJECT OF THE INVENTION

It is therefore an object of the invention to replace these classical therapies and to boost or even to monopolize the redox potential of cells with a malfunctioning metabolism.

SUMMARY OF THE INVENTION

This objective is accomplished owing to the fact that a thiol derivative of glutathione

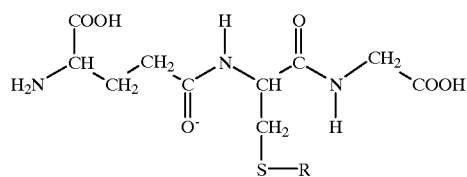

is used as glutathione derivative.

Due to the central molecular biological significance of the reduced glutathione in a physiologically appropriate, intracellular concentration, all of the following physiological, biochemical and vital cell functions are explainable as being dependent on the intracellular glutathione status (G—SH>mixed disulfides>G—S—S—G) alone.

Redox potential

Optimum ability of all enzyme reactions (active center as well as allosteric centers of an enzyme molecule) to work.

Preservation of the integrity of all biological membranes (cell and cell organelle membranes).

Among other reasons, this is also particularly important for optimizing the function of all structure-bound enzymes, for membrane carrier mechanisms, for the function and allosteric specificity of all cell receptors, etc.

Cofactor and reduction potential of many enzymes, especially of those, which are connected with the detoxification.

For the regulation and normalization of the complex space-time pattern of cell growth and cell differentiation processes.

For the prevention, attenuation and termination of free radical reactions and free radical chain reactions in living systems, etc.

Accordingly, the physiologically intracellular concentration of reduced glutathione is a primary prerequisite for all basic cell functions.

For this reason, the normalization of the intracellular G—SH concentration is of causal, therapeutic significance for the treatment and prophylaxis of many diseases, of most diseases, even of different etiology and by phenomenologically different pathobiochemical noxious agents.

Figure 1:
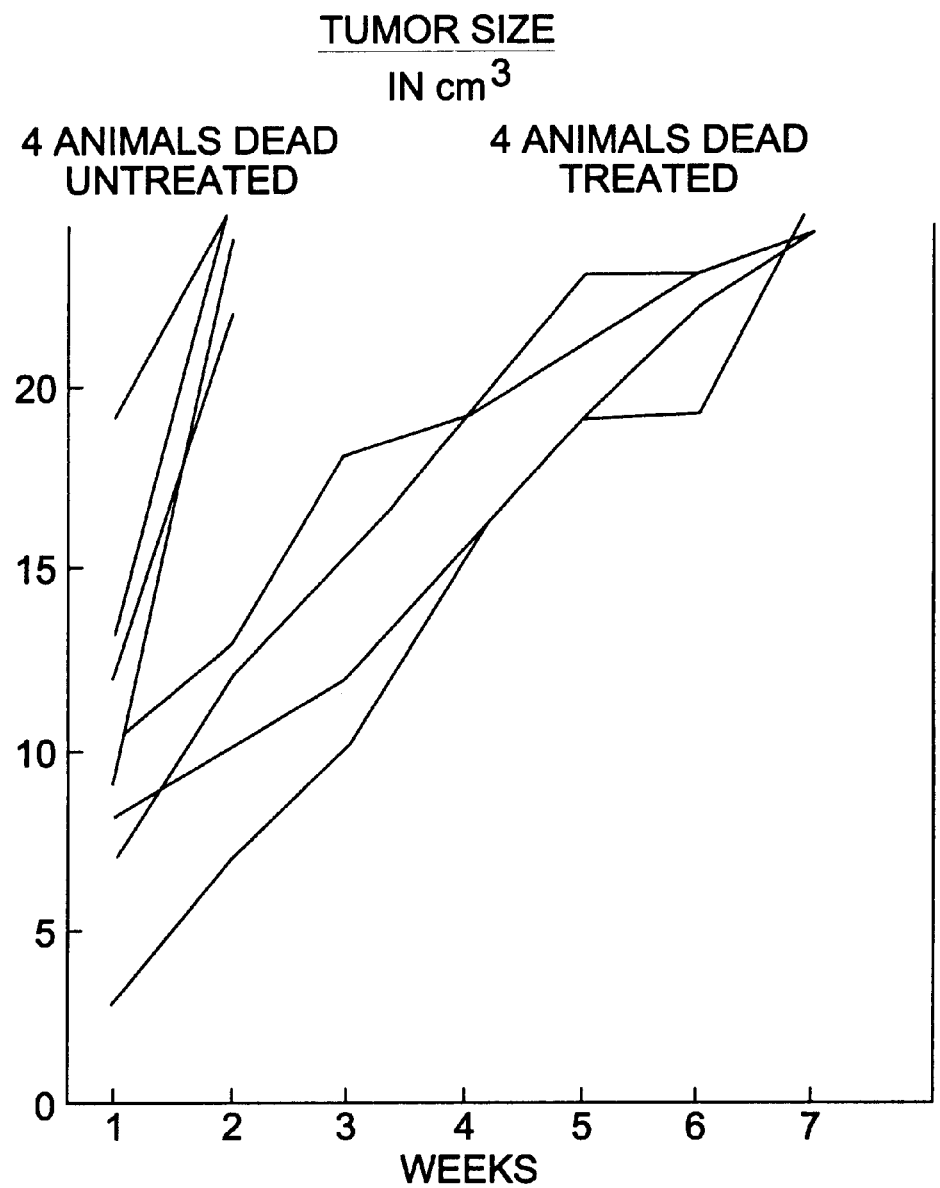
FIG. 1 is a graph illustrating the growth of a transplanted tumor ($cm^3$) in eight mice, four treated with reduced glutathione and four untreated, as a function of time (weeks).

A reliable basic therapy to normalize a cell metabolism, injured by different noxious agents, becomes possible for the first time through the following glutathione derivatives, which are readily bioavailable and effective:

2.) methyl thioether of gamma-glutamyl-cysteinyl-glycine
3.) ethyl thioether of gamma-glutamyl-cysteinyl-glycine
4.) monoacetyl thioester of gamma-glutamyl-cysteinyl-glycine
5.) monophosphate thioester of gamma-glutamyl-cysteinyl-glycine All trials on cells, animals and persons for the indications given under 10.) to 27.) could be detected for the first time with reduced glutathione and with the glutathione derivatives 2.) to 5.) and the combinations 6.) to 9.).

The following are the essential advantages of the pharmaceutical, therapeutic application of the derivatives of the reduced glutathione (GSH), which are defined in 2.) to 5.) and described here for the first time, in diseases of man and animals, and also the objects of the invention:

A) The good ability of these derivatives 2.) to 5.) to penetrate through biological membranes, as a result of which an effective intracellular therapy with glutathione, with all its positive physiological consequences, becomes possible.

B) Protection of the SH group of glutathione, which is so important for the therapeutic effects, on the path through biological compartments up to the desired site of action.

C) No inhibition of the enzymes (gamma-glutamylcysteine-synthetase, the regulation enzyme by glutathione in the sense of a negative feedback; glutathione synthetase) involved in the endogenous glutathione biosynthesis. As a result, the possibility exists of a glutathione (G—SH) substitution for the intracellular space without inhibition or blockage of a still possible (depending on the degree of cell damage) endogenous glutathione biosynthesis in the path of a competitive and/or allosteric inhibition.

D) The pharmaceutical, therapeutic application of the glutathione derivatives defined in 2.) to 5.) also does not lead to any inhibition of the endogenous glutathione biosynthesis in healthy cells.

So that a therapeutical usable glutathione therapy is possible in therapeutically effective and justifiable intracellular concentrations over different application paths (oral-enteral, nasal, buccal, sublingual, per inhalationem, vaginal, rectal, intracutaneous, subcutaneous, intramuscular, intravenous, per infusionen, intraarterial), the molecule, with its SH group intact, must be effective within the cell and must readily be able to pass through the membrane.

This essential requirement for being able to use glutathione (G—SH) on a relatively broad scale becomes possible for the first time through the derivatives described and investigated in Positions 2.) to 5.).

Because of the basic effect of G—SH in suitable intracellular concentrations of normalizing basic mechanisms of cell metabolism, the described derivatives 2.) to 5.) can be used by themselves and/or in combination with themselves or with preparations 6.) to 9.):

For all inflammatory (also allergic and autoaggressive), chemically toxic, physically toxic (also radiation damage due to electromagnetic waves and/or corpuscular radiation), infectiously toxic, cell, tissue and organ damage; as well as for pathological infiltrations, depositions on and in tissue; for atrophies, hypertrophies, dysplasias to anaplasias, also for benign tumors and for malignant neoplasias with and without metasticization.

For denaturing processes on and with biological molecules, in normotrophic and bradytrophic tissues.

For immune weakness of any origin.

For cancer prophylaxis and for adjuvant cancer treatment within the scope of other cancer therapies and those with chemotherapeutic agents or with a radiation treatment.

From this arise, in particular, possibilities for therapeutic use as drugs, which are characterized in claims 1.) to 27.).

Moreover the increase in oxygen radicals, which is caused by a lack of reduced glutathione and can destroy molecular and cell structure and thus bring about malignant degeneration or cell death, can also be compensated for optimally.

The laboratory-tested, first therapeutic application of reduced glutathione and/or its thiol derivatives as drug in man and mammals represents a completely new therapy in mental inception and in practice in order to be able to treat, depending on the dose, the following indications or diseases, which are listed by way of example and not by way of limitation.

The prevention of a "hyperoxidation" by a physiological adjustment of the redox potential of cells and tissue using the reduced glutathione and/or its thiol derivatives as a therapeutic agent is a fundamentally new method for the treatment of many diseases, including the prophylaxis and treatment of malignant tumors.

The glutathione reductase, a flavoprotein fulfilling the function of the electron transfer agent, adjusts the concentration ratio of (G—SH) to (G—S—S—G) to a value of about 400:1 in all human cells. This value reflects the vitality and the physiological ability of a cell to function.

The biosynthesis of glutathione from the three amino acids, glutamic acid, cysteine and glycine takes place intracellularly and independently of DNA with intervention of two enzymes, the gamma-glutamyl-cysteine synthetase and the glutathione synthetase with consumption of 2 moles of adenosine triphosphate (ATP).

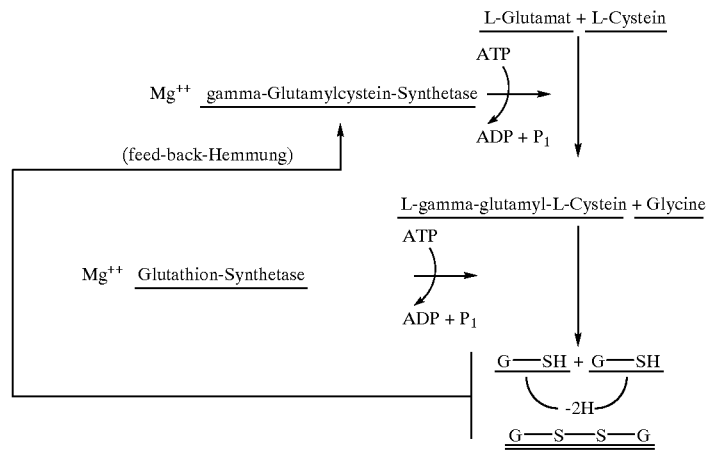

The relatively unusual peptide bond over the gamma carboxyl group of the glutamic acid prevents an uncontrolled degradation of the glutathione molecule by peptidases. Reduced glutathione is a white, crystalline substance, which melts at 192°–195° C. with decomposition. It has a molecular weight of 307.33. Reduced glutathione is readily soluble in water and physiological salt solution and soluble in ethanol.

The "extended" molecule G—SH has a length of 15 Å. Despite slight differences in the absorpthon behavior of some functional groups of the glutathione molecule, a reliable absorption behavior with an absorption maximum at 230 nm can be detected.

The pK values for SH are at 9.66, for $NH_3^+$ at 8.66, for $COOH_{(1)}$ at 3.53 and for $COOH_{(2)}$ at 2.12.

SH groups, also those of reduced glutathione (G—SH), are very reactive radical scavengers, in that they give up their hydrogen to carbon, oxygen and nitrogen radicals. Aside from the function of the G—SH/G—S—S—G system as a basic redox system of living systems, the previously addressed hydrogen transfer aspect of the reactive SH group has a particularly important significance for the comprehensive biological role of the G—SH.

Possible one-electron transfer process are shown in the following

A. Hydrogen Abstraction Thiyl Radical
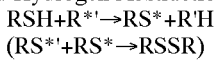
(RS*'+RS*→RSSR)

B. Photoionization
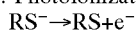

One-Electron to a Metal Ion
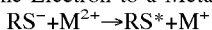

D. One-Electron Reduction of Disulfides
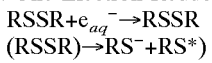
(RSSR)→RS⁻+RS*)

Two-electron transfers are also possible, for example, when two G—SH are converted into one G—S—S—G.

The biological half-life time of glutathione is different in different human tissue. In erythrocytes it is about 100 hours, in the brain about 70 hours, in the eye lens about 30 hours and in the liver only about 4 hours!

Aside from the one- and two-electron transfer, the formation of mixed disulfides and the thiol-disulfide exchange reactions are also possible with glutathione.

Glutathione is a component of many important enzymes, such as glutathione peroxidase or glutathione reductase. Glutathione peroxidase protects intracellularly, for example, against many of the hydroperoxides formed in different ways. It does so by its ability to reduce these in close cooperation with catalases to water.

The selenium-dependent glutathione peroxidase splits $H_2O_2$ as well as organic peroxides (ROOH). A second glutathione peroxide, which is not selenium dependent, exclusively splits organic peroxides.

The glutathione reductase intracellularly takes care of the physiological concentration ratio of G—SH to G—S—S—G, which has already been discussed previously. The intracellular G—SH concentrations are of the order of 1 to $50 \times 10^{-4}$M; the intracellular G—S—S—G are only of the order of 6 to $200 \times 10^{-6}$M.

Approximately 30% of the G—SH is present in the form of mixed disulfides (prot-S—S—G).

The tasks of glutathione in the intermediary metabolism of man are especially:
1.) redox system
2.) thiol-disulfide exchange reaction with enzymes and structure proteins
3.) detoxification of alkylating drugs and chemicals
4.) amino acid transport through cell membranes
5.) chelate formation and bonding
6.) protection of "free" radicals; energy absorption of "free" radicals
7.) reaction partners of d-fined enzyme reactions:
   glutathione peroxidase,
   glutathione reductase;
   glutathione-S-transferases, such as glutathione-S-aryl transferases,
glutathione-S-alkyl transferases,
glutathione-S-epoxide transferases, as well as
glutathione-dihydroascorbate reductase, etc.

Taking the functions listed above into consideration, the following features are characteristic of a therapy with reduced glutathione:

1.) improvement in all specific cell functions due to the normalization of the redox potential and an optimization of the protection against destruction of important biomolecules and cell structures by hyperoxidation, as well as protection against lipid peroxidation, etc.

2.) optimization of the function of many cell enzymes by adjusting the redox potential to a value optimum for the cell, partly by forming mixed disulfides.

3.) normalization of the mitotic power of a cell by adjusting the redox potential, thereby acting in a tumor-protective and tumor-therapeutic manner.

4.) carrying out enzyme reactions, since these can take place only if sufficient glutathione is available. Glutathione is a component of many defined enzymes, such as glutathione peroxidase, glutathione-S-transferases, glutathione dihydroascorbate reductase.

5.) normalization of all physiological cell functions, which are possible due to the action of glutathione.

The positive effects are produced not only by reduced glutathione, but also by different derivatives of the reduced glutathione, especially by the monomethyl ester of the reduced glutathione, by the monoethyl ester of the reduced glutathione, by the monoacetyl derivative of the reduced glutathione and by the monophosphate ester of the reduced glutathione.

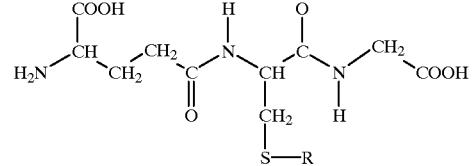

1.1.) methyl glutathionyl thioether $R=CH_3$
1.2.) ethyl glutathionyl thioether $R=CH_2—CH_3$
1.3.) monoacetyl thioester of glutathione $R=COCH_3$
1.4.) monophosphate thioester of glutathione $R=PO_3H_2$
(TRANSLATOR'S NOTE: the last two definitions for R should be checked)

Excellent tolerance and increased effectiveness is shown by combination preparations of the reduced glutathione as well as of the glutathione derivatives described above in conjunction with substances, which contain covalently bonded semiconductor elements such as silicon, selenium or germanium. The same is true for combination preparations with vitamins such as vitamin A, vitamin E or the provitamin, beta carotene, as well as amino acids such as L-cysteine or L-methionine. The pure, reduced glutathione, as well as different derivatives of the reduced glutathione and several of the substances named may be contained in such combination preparations. The preparations are suitable for the treatment of numerous diseases in a wide range of indications.

Range of Indications

Treatment of carcinoses of any origin, also for malignant diseases of the blood cells and their precursors Substitution and regulation of the metabolism when carrying out other cancer therapies, chemotherapies, radiation therapies and/or naturopathic therapies.

Prophylaxis and treatment of metastases within the scope of malignant tumor diseases.

Hepatopathies, especially acute and chronic hepatitis, such as chemically-toxic and infectious-tocic hepatitis, viral, rickettsial, bacterial or protozoal hepatitides, and chronic-aggressive hepatitis, fatty degeneration of the liver, fatty cirrhosis and liver cirrhosis of any origin.

Disorders of the immunological defense function in the area of natural killer cells, monocytes, macrophages, granulocytes, T and B lymphocytes, plasma cells, as well as disorders of the complement factors and antibody synthesis.

Complex disorder of the lymphokine biosynthesis in T helper cells, macrophages and other cells.

Treatment of cardiomyopathies of any origin, also in conjunction with other therapies, all forms of coronary diseases, angina pectoris, myocardial infarction prophylaxis as well as emergency therapy of myocardial infarction in conjunction with other emergency drugs.

Acquired as well as inherited disorders of skeletal muscles.

Neurological disorders of inflammatory, allergic or degenerative origin.

All forms of blood cell diseases, anemias, leukopenias, lymphopenias and thrombocytopenias.

Prophylaxis for injuries to the lens of the eye, toxic disorders of the retina and the vitreous body, as well as cataract prophylaxis.

All forms of hyperoxidation or oxidative stresses, for example, within the scope of the use of oxygen therapies or therapies with activated oxygen steps (oxygen radicals) as well for protection during use of hyperbaric oxygen therapy or oxygen multistep therapy and in the case of ozone therapies and HOT therapies.

Intoxications, which lead over free radical chain reactions to biomolecule or tissue injury in the human organism.

Accompanying therapy for treatment by radiation or with cytostatic drugs, as well as for the prevention or attenuation of indisposition, nausea, etc.

After anesthesias, especially after general anesthesias in patients with heart or liver damage.

Intoxications with xenobiotic agents, especially with toxic trace elements and with heavy metals.

Proliferation and differentiation disorders of epithelial, endothelial and mucous membrane tissues.

Treatment of pathophysiological arterioscleroses and those of different origins.

Basic and adjuvant treatments of allergies.

Treatment of impotentia cceundi and impotentia generandi, as well as fertility disorders and sexual potency disorders of any origin. Also in the case of premature aging, detrition of any tissue due to age and as prophylaxis in the case of activities, which lead to premature aging or to attrition of organs.

Pharmaceutical Forms

The reduced glutathione and its thiol derivatives can be administered for therapy in the following forms:
1.) intravenously, also as infusion,
2.) intramuscularly,
3.) intracutaneously and subcutaneously,
4.) orally,
5.) nasally, bucally, sublingually,
6.) per inhalationem,
7.) vaginally and
8.) rectally.

The intravenous injection or infusion is mostly recommended for serious or acute diseases, the infusion being preferred especially for higher dosages over a longer period of time.

Suitable as a basis for the preparation of the infusion solution in pure form or as a mixture is a physiological salt solution (0.9% NaCl in water), Ringer's solution or a monosaccharide solution (5% glucose, 5% levulose). To protect the free SH group of the reduced glutathione, it should be made certain that the pH of the solution is within the range of 6.8 to 7.4.

During storage, reduced glutathione and its derivatives should be protected against light, so that dark glass is recommended for the ampoules.

During an intravenous administration, a maximum amount of glutathione in reduced form can be supplied directly into the intravasal space of the organism. With other forms of administration on the other hand, it must be taken into consideration that the substance oxidizes partially while being absorbed.

Nevertheless, the subcutaneous, intramuscular, intraarterial and also the oral forms of administration are of advantage for the long-term treatment. Oral administration is possible in the form of tablets, granulate, capsule, powder or drops. It is self-evident that a decrease in effect due to oxidative reactions may arise in the case of oral-enteral administration as well as upon administration by inhalation.

Provided that the medical prerequisites are fulfilled, intratumoral and also intraperitoneal admini3tration are possible.

Likewise, it is possible to administer reduced glutathione or its derivatives in the form of suppositories, that is, rectally or vaginally with the limitation of a slightly inferior systematic (TRANSLATOR'S NOTE: should this perhaps be systemic?) but relatively good local bioavailability.

In special cases of wounds that do not heal well, such as burns, frostbites or gangrenous ulcers, administration in the form of ointments, spray or as liquid also comes into consideration and leads to good therapeutic results.

The different dosage and pharmaceutical preparation for the respective form of administration corresponds to the bioavailability, biological tolerance, therapeutic safety and the harmlessness at the correct dosage, which are different for each application.

Dosage

The therapeutic dosage for man, which has proven to be nontoxic in animal experiments with small animals such as gray mice, Wistar rats and rabbits, falls within the range of 2–5 mg/kg of body weight in man for a single dose administered by a slow, intravenous injection, the injection volume being 5 mL and containing 150 mg of reduced glutathione.

As intravenous infusion, daily dosages of up to 20 mg/kg of body weight and, in special cases, even higher dosages can be administered as intravenous infusion in a carrier volume of 250 ml. At a dosage of 20 mg/kg of body weight, the minimum infusion time should not be less than 30 minutes.

Injection and infusion solutions, which contain reduced glutathione, should not be mixed with other drugs. Fresh infusion solutions should always be prepared before an administration and they are intended for immediate use.

Basically, a dose ranging from 2 to 20 mg/kg of body weight is recommended as daily dose, the exact dose depending on the individual circumstances within the scope of the disease. Only in the case of carcinoses with metastases and a total mass of tumors in excess of 100 g may daily dosages higher than 20 mg/kg of body weight find application.

The duration of the therapy depends on the basic disease that is to be treated. If the therapy lasts longer than 4 weeks, the trace element level in the serum should be checked. For the quantitative determination, it is recommended that the zinc content of the serum be determined as a screening test parameter.

The potassium and magnesium contents can serve as therapeutic guiding parameters for the serum electrolytes.

Pharmaceutical Preparation

The injectable solutions of reduced glutathione and/or its thiol derivatives should be present as heavy-metal-free solutions in sterile and pyrogen-free water with a conductivity of less than 5 $\mu$S. It is recommended that the solutions be kept in dark glass ampoules.

Infusion solutions should always be prepared fresh by injecting the ampoule contents into the infusion carrier solutions.

When selecting adjuvants and fillers for all other forms of preparation, care must be taken that these cannot enter into any undesirable reactions with the free SH groups of the reduced glutathione, so that the active ingredient can be prepared, stored and administered unchanged in the respective form in which it was prepared.

Experimental Results

In Vitro Exeriments 1.1) In vitro experiment with human erythrocytes to improve and normalize the redox behavior:

Human venous blood (10 mL) was taken from each of 20 patients with different diseases and prevented from clotting by the addition of heparin. As a parameter for the optimum erythrocyte function, the content of intraerythrocytic reduced glutathione was determined before and after incubation with 0.5 mg of reduced glutathione at 37° C. over a period of 30 minutes.

n=20 (average value ani standard deviation are given)
blank: 1.50±0.47 mU
value of incubation: 1.99±0.15 mU 1.2) In vitro experiment on cell systems of human erythrocytes Under the same conditions as those for the experiment described above, the enzymes, glucose-6-phosphate dehydrogenase and glutathione reductase, from the erythrocytes of 22 patients, were investigated in vitro.

n=22 (average value and standard deviation are given)
Blanks:
glucose-6-phosphate dehydrogenase 148±22 mU/$10^9$ erys.
glutathione reductase 9.5±0.8 U/$10^{11}$ erys.
Values After Incubation:
glucose-6-phosphate dehydrogenase 179±16 mU/$10^9$ erys.
glutathione reductase 11.3±1.2 U/$10^{11}$ erys.

In Vivo Experiments 2.1) Animal Experiments with rabbits to improve and/or normalize the redox status of the blood:

In 5 different rabbits, the following parameters were measured by the method and with the instrument of VINCENT in 30 experiments in venous blood:

Ohm's resistance: r
redox potential $E_H$ or electron potential: $rH_2$
pH

The values were measured in the venous blood of the ear after a defined oxygen deficiency stress.

| n = 30 (average value and standard deviation are given) | |
|---|---|
| r = 199 ± 12 ohm/cm² | Values after stress without |
| pH = 7.38 ± 0.21 | administration of |
| rH₂ = 24.9 ± 2.3 | reduced glutathione |

After that, reduced glutathione was administered to the animals in an amount of 10 mg/kg of body weight.

The following values were determined 5–10 minutes after the glutathione one was administered:

| r = 202 ± 14 ohm/cm² | Values after administration |
|---|---|
| pH = 7.15 ± 0.16 | of reduced glutathione |
| rH₂ = 21.8 ± 0.95 | and stress |

Boundary conditions: Temperature of 20° C., air pressure of 767 mm Hg.

2.2) Self-experiment on man to improve and/or normalize the redox status of the blood:

After a defined oxygen deficiency stress, the same parameters were determined in human blood as in the trial described above. In all 50 trials were carried out on different days

| n = 50 (average value and standard deviation are given) | |
|---|---|
| r = 197 ± 14.5 ohm/cm² | Values after stress without |
| pH = 7.41 ± 0.18 | administration of |
| rH₂ = 26.3 ± 2.1 | reduced glutathione |

After that, glutathione was slowly administered intravenously in an amount of 600 mg.

The following values were determined 10 minutes after the administration of reduced glutathione:

| r = 204 ± 12.3 ohm/cm² | Values after administration |
|---|---|
| pH = 7.23 ± 0.11 | of reduced glutathione |
| rH₂ = 23.1 ± 1.4 | and stress |

Boundary conditions: Temperature of 20° C., air pressure of 758–770 mm Hg.

2.3) Experiment with 8 healthy gray mice after transplantation of a malignant tumor from man.

The growth of the tumor as a function of time is shown in FIG. 1.

After $10^6$ cells of a malignant melanoma were transferred from man to each of 8 healthy gray mice, four animals that had not been treated with reduced glutathione (control group) died within 8–14 days. Four animals, which were treated three times per week with 250 mg of reduced glutathione (test group), showed a distinctly slower tumor growth and survived up to the sixth week. 2.4) Experiment with 40 healthy gray mice after transplantation of a malignant melanoma from man.

Forty healthy gray mice were inoculated with $10^6$ malignant melanoma cells each. Ten untreated control animals died within a period of 8–12 days.

Before the start of the series of experiments, 30 animals were treated three times per week with 300 mg reduced glutathione. Of these animals, three died within 15 days, a further five within 20 days and a further seven within 30 days.

Fifteen animals, that is, 50% of the animals treated with reduced glutathione, survived the period of observation, which lasted for 30 days after inoculation with regressive tumor cells. III.1 Experiment with 40 healthy gray mice after transplantation of a malignant melanoma from man.

Tumor Size
in cm³

Experiment No. III.1) Transfer of $10^6$ cells of a malignant melanoma an to each of 8 health gray mice.

Four untreated animals died from this transplanted tumor within a period of 8–14 days. Four animals, treated 3 times per week with 250 mg of reduced glutathione, showea a slower tumor growth and survived up to the seventh week.

I claim:

1. A method for increasing or maintaining intracellular concentration of reduced glutathione in a subject, comprising administering to said subject a thiol derivative of glutathione of the formula

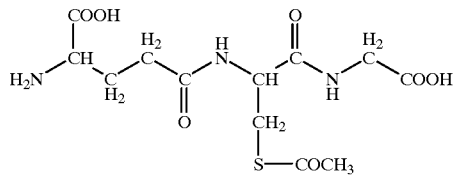

or a pharmaceutically acceptable salt thereof in an amount effective to increase or maintain the intracellular concentration of glutathione.

2. The method of claim 1, wherein said subject has deficient intracellular levels of reduced glutathione.

3. The method of claim 1, wherein said subject is at risk of developing deficient levels of intracellular reduced glutathione, and wherein said thiol derivative of glutathione is administered prophylatically.

4. The method of claim 1, further comprising administering at least one vitamin selected from the group consisting of vitamin A, vitamin E, beta carotene, vitamin C and mixtures thereof in combination with said thiol derivative.

5. The method of claim 1, further comprising administering at least one element selected from the group consisting of silicon, selenium, germanium and mixtures thereof in combination with said thiol derivative.

6. The method of claim 1, further comprising administering at least one amino acid in combination with said thiol derivative.

7. The method of claim 1, comprising administering said thiol derivative orally.

8. A method for preventing the onset of a progressive imbalance of the ratio of intracellular concentrations of reduced glutathione and oxidized glutathione in a subject, comprising administering to said subject a thiol derivative of glutathione of the formula

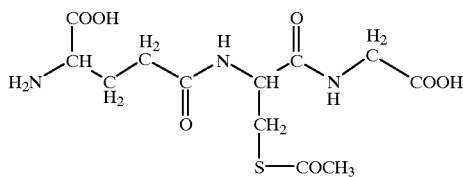

or a pharmaceutically acceptable salt thereof in an amount effective to prevent the onset of an imbalance of intracellular concentrations of reduced glutathione and oxidized glutathione.

9. A composition for raising or maintaining the intracellular concentration of glutathione in a subject, comprising a thiol derivative of glutathione of the formula

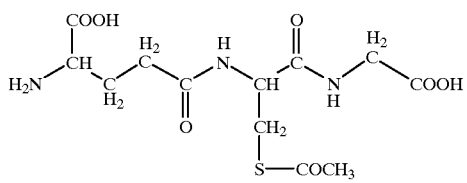

or a pharmaceutically acceptable salt thereof and a pharmaceutically acceptable carrier.

10. The composition of claim 9, further comprising at least one component selected from the group consisting of:

at least one vitamin selected from the group consisting of vitamin A, vitamin E, beta-carotene, vitamin C and mixtures thereof;

at least one element selected from the group consisting of silicon, selenium, germanium, and mixtures thereof; and at least one amino acid.

* * * * *

UNITED STATES PATENT AND TRADEMARK OFFICE
CERTIFICATE OF CORRECTION

PATENT NO. : 6,030,950
DATED : February 29, 2000
INVENTOR(S) : Ohlenschläger It is certified that error appears in the above-identified patent and that said Letters Patent is hereby corrected as shown below:

Title page, item [76], in the Inventor's address, "Köigstein" should read --Königstein--.

Title page, item [63], in the Related U.S. Application Data, line 10, "Jul. 16, 1992" should read --Jul. 11, 1991--.

Signed and Sealed this

Third Day of April, 2001

Attest:

NICHOLAS P. GODICI

*Attesting Officer*  *Acting Director of the United States Patent and Trademark Office*